United States Patent [19]

Knifton

[11] 3,933,884

[45] Jan. 20, 1976

[54] PROCESS FOR PREPARING THIOL ESTERS

[75] Inventor: John F. Knifton, Poughquag, N.Y.

[73] Assignee: Texaco Inc., New York, N.Y.

[22] Filed: Oct. 10, 1973

[21] Appl. No.: 405,190

[52] U.S. Cl. .......................... 260/455 R; 252/429 R
[51] Int. Cl.² ..................................... C07C 153/09
[58] Field of Search ................. 260/410, 455, 455 R

[56] References Cited
UNITED STATES PATENTS

| | | | |
|---|---|---|---|
| 2,863,911 | 12/1958 | Büchner et al. ..................... | 260/455 |
| 2,876,254 | 3/1959 | Jenner et al. ........................ | 260/410 |
| 3,161,672 | 12/1964 | Zachry et al. ..................... | 260/455 R |
| 3,176,038 | 3/1965 | Zachry et al. ..................... | 260/455 R |
| 3,660,439 | 5/1972 | Schell ................. | 260/410 |
| 3,681,415 | 8/1972 | Schell ................. | 260/410 |
| 3,700,706 | 10/1972 | Butter ................. | 260/410 |

*Primary Examiner*—Lewis Gotts
*Assistant Examiner*—D. R. Phillips
*Attorney, Agent, or Firm*—T. H. Whaley; C. G. Ries; Bernard Marlowe

[57] ABSTRACT

This invention concerns the preparation of linear saturated and unsaturated aliphatic thiol esters by the catalytic addition of carbon monoxide plus a sulfur containing nucleophile having a mobile hydrogen atom, to the carbon-to-carbon unsaturated bond of a 1-alkene or 1-alkyne, using homogeneous noble metal, bimetallic catalyst complexes.

7 Claims, No Drawings

PROCESS FOR PREPARING THIOL ESTERS

SUMMARY OF THE INVENTION

This invention concerns the preparation of linear aliphatic thiol esters by the catalytic addition of carbon monoxide plus a sulfur containing nucleophile having at least one mobile hydrogen atom to the carbon-to-carbon unsaturated bond of a 1-alkene or 1-alkyne substrate, using homogeneous noble metal, bimetallic catalyst complexes.

More particularly this invention relates to synthesis of two known classes of thioesters, linear saturated and unsaturated thiol esters by the catalytic carbonylation of 1-alkenes and 1-alkynes, respectively, in the presence of the aforementioned noble metal catalyst complexes.

BACKGROUND OF THE INVENTION

Linear saturated aliphatic thiol esters as defined throughout this application have the formula:

$$RCH_2CH_2COSR'$$

wherein R is selected from the group consisting of hydrogen and alkyl radicals containing from zero to 28 carbon atoms and R' is selected from the group consisting of alkyl and aryl radicals containing up to 10 carbon atoms, including phenyl ($C_6H_5$) and alkylated phenyl wherein the alkyl groups contain from 1 to 4 carbon atoms.

Linear unsaturated aliphatic thiol esters as defined herein have the formula:

$$RCH = CHCOSR'$$

wherein R and R' have the same definitions defined supra.

The usual preparation of saturated thiol esters is by the reaction or a mercaptan with an acid chloride frequently in the presence of pyridine. Sometimes anhydrides are substituted for the acid chlorides. Other preparations include the reaction of an acid chloride with a metal mercaptide, or the reaction of a thio acid salt and an alkyl halide among other methods. These thiol esters may be treated with amines to form N-substituted carboxamides and a mercaptan or may be desulfurized with fresh Raney nickel to produce an alcohol (i.e. $RCOSR' \rightarrow RCH_2OH$) etc.

It is noteworthy that the synthesis of saturated and unsaturated thiol esters from 1-alkenes or 1-alkynes with "classical" carbonylation catalysts, such as the Reppe nickel carbonyl catalysts, gives mainly branched-chain thiol esters rather than the more desirable linear thiol esters, in moderate yields, and under fairly stringent reaction conditions. For example, the synthesis of ethyl thiol-α-methyl octanoate in 15% yield from octene*.

*W. Reppe and H. Kroper, Ann.

In both types of products, linear saturated and unsaturated thiol esters, the methods of synthesis are not entirely satisfactory, for example yields are poor or erratic, purification is difficult and/or reaction conditions are rigorous, and in many instances predominantly branched-chain rather than linear thiol esters are produced.

In this invention, noble metal catalysts, particularly ligand-stabilized noble-metal halide catalysts, in conjunction with Group IVB metal halide co-catalysts (both types of catalysts to be described subsequently), are used to catalyze the addition of carbon monoxide into the carbon-to-carbon unsaturated bonds of 1-alkenes or 1-alkynes in the presence of a sulfur containing nucleophile having a mobile hydrogen atom, preferably a mercaptan, to produce linear saturated or unsaturated thiol esters. For instance, the synthesis of a typical linear saturated thiol ester, such as ethyl thioloctanoate, is shown below:

$$CH_3(CH_2)_5CH = CH + CO + C_2H_5SH$$
$$\rightarrow CH_3(CH_2)_6CH_2COSC_2H_5$$

Similarly, the preparation of an illustrative unsaturated thiol ester is as follows:

$$HC \equiv CH + CO + C_3H_7SH \rightarrow H_2C = CHCOSC_3H_7$$

It should be noted that the instant invention is also distinguishable over related co-assigned cases* in that:

1. In the related cases, while the same classes of homogeneous noble metal catalysts are used in conjunction with carbon monoxide and unsaturated substances, sulfurcontaining nucleophilic reactants are employed in this case rather than the oxygen-containing nucleophilics such as alkanols, phenols, and water described in the previous cases.

*Ser Nos. 233,014 and 233,015

PROCESS DESCRIPTION

In the broad practice of this invention, unsaturated aliphatic substrates are converted to linear saturated and unsaturated aliphatic thiol esters of carboxylic acids in good yield and relatively uncontaminated with branched chain by-products by a process of:

a. admixing each mole of at least one unsaturated aliphatic substrate selected from the group consisting of 1-alkenes and 1-alkynes containing 2 to 30 carbon atoms with at least a molar equivalent of mercaptan co-reactant, in the presence of at least stoichiometric quantities of carbon monoxide, and in the presence of at least a catalytic amount of a homogeneous noble metal catalyst consisting essentially of two components: (1) a noble metal halide selected from the group consisting of platinum and palladium halides, in combination with (2) Group IVB metal halide co-catalysts, in the absence of substantial quantities of oxidizing agents and water to form a reaction mixture, pressurizing and b. heating said pressurized, substantially oxidizer-free water-free reaction mixture at elevated temperatures until conversion of the unsaturated aliphatic substrate contained in said reaction mixture to the aliphatic thiol ester takes place, and c. optionally isolating the aliphatic thiol esters that are contained therein.

Preferably the noble metal catalyst of this invention consists of three components: (1) a platinum(II) or palladium(II) halide stabilized with (2) one or more Group VB donor ligands, and (3) in combination with a Group IVB metal halide co-catalyst such as tin(II) halides, tin(IV) halides and germanium(II) halides.

In order to present the inventive concept in the greatest possible detail as to promote its understanding, the following supplementary disclosure is submitted:

A. Process Sequence and Variations. In general, the components of the aforementioned reaction mixture, including optional inert solvent, thiol co-reactant, unsaturated aliphatic substrate and catalyst may be added in any sequence as long as sufficiently good agitation is provided to assure the formation of a homogeneous mixture. For example, the following represent some variations insofar as the catalyst, sequence of CO, and heating, that may be made without departing from the inventive process. These modifications include:

1. The catalyst may be preformed.

2. To minimize stability problems with the homogeneous catalysts, it is preferred to form the catalyst in situ, usually by first adding the Group IVB metal halide, in anhydrous form, in excess over what is required by stoichiometry, followed by the addition of noble metal halide complex such as $PdCl_2[P(C_6H_5)_3]_2$.

3. A third variation is that the catalyst is prepared in situ by adding as separate components of the reaction mixture the noble metal halide, such as palladium(II) chloride, the Group VB donor ligand, such as triphenylphosphine, and the Group IVB metal halide co-catalysts such as tin(II) chloride.

After using variation (1), (2) or (3), the reactor, containing catalyst, agitated deoxygenated inert solvent and thiol co-reactant is sealed, carbon monoxide is added to the agitated system, which is heated to about the reaction temperature and to autogenous pressures. After a homogeneous system is obtained, the unsaturated aliphatic substrate such as 1-heptene, is added, and the pressure is raised until the desired psig is obtained. At the end of a sufficient reaction time, either empirically determined beforehand, or determined by monitoring samples withdrawn for analysis during the reaction, the reaction is terminated, cooled, vented and worked up.

4. A substantial process variation that can be employed when the catalyst is formed in situ in an inert solvent is to heat the catalyst containing solution to temperature under an inert atmosphere or a slightly elevated pressure of CO, and then to add the mercaptan co-reactant, the unsaturated aliphatic substrate and carbon monoxide with efficient agitation and to maintain the CO pressure in the reactor until the thiol ester is formed.

B. Homogeneous Noble Metal Catalyst — The homogeneous noble metal catalyst of this invention consists of at least two components: (1) a noble metal halide, selected from the group consisting essentially of platinum and palladium halides, and (2) a Group IVB metal halide co-catalyst. Preferably the homogeneous noble metal catalyst consists of three components: (1) a noble metal halide, selected from the group consisting of platinum(II) and palladium(II) halides stabilized with (2) one or more Group VB donor ligands, and in combination with (3) a Group IVB metal halide co-catalyst.

Each Group VB donor ligand contains one or more donor atoms selected from Group VB of the Periodic Chart of the Elements (Advanced Inorganic Chemistry by F. A. Cotton and G. Wilkinson, 2nd Ed., 1966), preferably it contains one or more trivalent phosphorus or arsenic atoms. These Group VB donor atoms are bonded to hydrocarbyl radicals selected from the group consisting of aryl, alkyl, and substituted aryl radicals, which may contain up to 20 carbon atoms and need not be the same.

Illustrative of suitable Group VB donor ligands which may be used in combination with the noble metal(II) halide and the Group IVB metal halide to form active carbonylation catalysts for the preparation of unsaturated and saturated aliphatic thiol esters are:

$P(C_6H_5)_3$, $As(C_6H_5)_3$, $P(CH_3)_2(C_6H_5)$, $P(p-CH_3.C_6H_4)_3$, $P(p-Cl.C_6H_4)_3$, $P(o-CH_3O.C_6H_4)_3$, $P(p-CH_3O.C_6H_4)_3$, $P(OC_6H_5)_3$, $P(C_6H_{11})_3$, $As(n-C_4H_9)_3$, $P[(p-CH_3.C_6H_4)(C_6H_5)_2]$, $(C_6H_5)_2P(CH_2)_2P(C_6H_5)_2$, $(C_6H_5)_2P(CH_2)P(C_6H_5)_2$, and $Sb(C_6H_5)_3$.

The Group IVB metal halides that may be used as co-catalysts in this invention include the halides of tin(II), tin(IV) and germanium(II). Illustrative examples include tin(II) chloride, tin(IV) chloride, tin(II) bromide and germanium(II) chloride. In certain cases, the anhydrous chlorides of the Group IVB metal halides are favored, with anhydrous tin(II) chloride being the preferred co-catalyst.

The following complexes are among the many ligand stabilized palladium(II)-Group IVB metal halaide complexes and ligand-stabilized platinum(II)-Group IVB metal halide complexes which can be used in the catalytic conversion of unsaturated aliphatic substrates to unsaturated and saturated aliphatic thiol esters:

$PdCl_2[P(C_6H_5)_3]_2—SnCl_2$, $PdCl_2[As(C_6H_5)_3]_2—SnCl_2$, $PdCl_2[P(OC_6H_5)_3]_2—SnCl_2$, $PdCl_2[P(p-CH_3O.C_6H_4)_3]_2—SnCl_2$, $PdCl_2[P(C_6H_5)_3]_2—GeCl_2$, $PdCl_2[P(p-Cl.C_6H_4)_3]_2—SnCl_2$, $PtCl_2[P(C_6H_5)_3]_2—SnCl_2$, $PtCl_2[As(C_6H_5)_3]_2—SnCl_2$ $PdCl_2[P(C_6H_5)_3]_2—SnCl_4$, and $PdCl_2[P(CH_3)_2C_6H_5]_2—SnCl_2$ In certain cases the Group VB donor ligand, typified by triphenylphosphine, is used in excess of the amount required for complex formation, and the Group IVB metal halide co-catalyst also in excess in order to obtain a stable and active catalyst.

C. Ratio of Noble Metal Catalyst to Unsaturated Aliphatic Substrate — Experimental work indicates that a molar ratio of up to 500 moles of unsaturated aliphatic substrates per mole of noble metal catalyst complex can be employed in most instances where unsaturated aliphatic substrates typified by 1-alkenes are used as the substrate. This molar ratio constitutes what is referred to as a catalytic amount. Much lower ratios (i.e. 25 moles of substrate per mole of noble metal catalyst) are not harmful but are economically unattractive. For this reason the preferred molar range varies from 50 to 200 moles of substrate per mole of noble metal catalyst.

D. Temperature required for Thiol Ester Formation — The temperature range which can be employed for ester formation is variable dependent upon other experimental factors including the substrate employed, the pressure, the concentration and the particular choice of catalyst among other things. Using 1-heptene as a typical unsaturated substrate and $PdCl_2—[P(C_6H_5)_3]_2—SnCl_2$ as a representative catalyst, the range of operability is from about 20° to 120°C when superatompsheric pressures of 2,000°–3,000 psig or higher are employed.

E. Pressure — Carbon monoxide pressures up to at least 3,000 psig lead to substantial conversion of the unsaturated aliphatic substrate to the corresponding thiol ester at temperatures of 20 to 120°C using $PdCl_2[P(C_6H_5)_3]_2—SnCl_2$ as catalyst and 1-heptene as the unsaturated substrate. Table II and Example 17 provide the supporting experimental data.

F. Reaction Times Required — As previously indicated in the analogous discussion on temperatures and pressures required in the reaction, experimental variables are important in arriving at reaction times. Generally substantial conversions (70% or higher) of the the substrates to the saturated or unsaturated thiol ester can almost always be accomplished within 20 hours with 4 to 8 hours representing the more usual reaction time interval.

G. Unsaturated Aliphatic Substrates - As used throughout this disclosure, this term refers to two related classes of unsaturated aliphatic substrates, wherein the unsaturation (double or triple bonds) in the substrate is only between carbon to carbon atoms. Illustrative of the two classes of unsaturated aliphatic substrates are those of the structures:

   A and

   B wherein R is selected from the group consisting of hydrogen and alkyl radicals containing zero to 28 carbon atoms.

Unsaturated alkenes of structure A are commonly known as α-olefins and include ethylene, propylene, 1-butene, 1-pentene, 1-hexene, 1-heptene, 1-octene, etc.

Unsaturated alkynes of structure B include the lowest member of the series commonly known as acetylene, as well as its homologues such as 1-propyne, 1-butyne and 1-pentyne.

H. Nucleophilic Co-Reactant — In order to prepare the saturated or unsaturated aliphatic thiol ester products, a sulfur-containing nucleophilic co-reactant, preferably a mercaptan, having a labile hydrogen, must be present in the reaction mixture with the unsaturated aliphatic substrate, carbon monoxide and catalyst. The mercaptan may be aliphatic or aromatic or cyclic and it can contain from 1 to 10 carbon atoms. Where the mercaptan is aromatic it can be alkylated with one or more alkyl groups containing 1 to 4 carbon atoms exclusive of the carbons of the aromatic rings. Suitable mercaptans include methyl mercaptan, ethyl mercaptan, propyl mercaptan, butyl mercaptan, pentyl mercaptan, hexyl mercaptan, heptyl mercaptan, cyclohexyl mercaptan, phenyl mercaptan (benzene thiol), benzyl mercaptan, ethyl benzene thiol and their homologues I. Carbon Monoxide Environment — Insofar as can be determined, the best selectivities and conversions of unsaturated aliphatic substrates to saturated or unsaturated aliphatic thiol esters can be obtained within a reasonable reaction time by using a substantially carbon monoxide gaseous atmosphere. However, particularly in continuous operation the carbon monoxide may be used in conjunction with from about 0 to 30% by volume of one or more inert gases such as nitrogen, argon, neon and the like without experiencing any substantial decrease in yield and selectivity. The amount of CO provided must be at least sufficient to satisfy the stoichiometry of the carbonylation reaction.

J. Inert Solvents — The novel reaction is run most conveniently in the presence of an inert diluent. A variety of solvents can be used, including aromatics such as benzene, toluene and xylenes, halogenated aromatics including o-dichlorobenzene and chloronaphthalene, ethers such as dimethyloxyethane and p-dioxane, ketones such as diethyl ketone and methyl isobutyl ketone, and halogenated paraffins including methylene chloride. Ketones such as acetone, methyl ethyl ketone and particularly methyl isobutyl ketone are the preferred solvents in the inventive process.

K. Selectivity as defined herein is the efficiency in catalyzing the desired carbonylation reaction relative to other undesired competing reactions, such as formation of the branched chain thiol ester; in this instance carbonylation to the linear aliphatic thiol ester derivative is the desired conversion. Selectivity is usually expressed as a percentile, and is calculated herein by determining the total amount of desired linear thiol ester product formed, divided by the total amount of thiol ester products which are formed, and multiplying the quotient obtained by 100.

L. Conversion as defined herein is the efficiency in converting the unsaturated aliphatic substrate to other products. Conversion is also expressed as a percentile and is calculated herein by dividing the amount of unsaturated aliphatic substrate (1-alkene or 1-alkyne) consumed during carbonylation* by the amount of unsaturated aliphatic substrate originally charged to the reactor and multiplying the quotient by 100.

*Carbonylation as used throughout this disclosure refers to addition of carbon monoxide plus a mercaptan to the carbon-to carbon unsaturated bond of the substrate alkene or alkyne.

M. By-Products — As far as can be determined, without limiting the invention or its novelty, the essence of the inventive process is carbonylation (the addition of carbon monoxide plus a mercaptan to carbon-to-carbon unsaturated bond of a 1-alkene or 1-alkyne). These reactions are catalyzed by the homogeneous noble metal catalysts of this invention. Quantitatively speaking, there are only relatively minor amounts of by-products (less than 30% by weight) of the total product content. These consist primarily of sulfides formed by the addition of the mercaptans only to the 1-alkenes and 1-alkynes.

Unless otherwise stated, all parts are by weight, all temperatures in degrees centigrade and all pressures in pounds per square inch gauge (psig.)

EXAMPLE 1

The Preparation of Ethyl Thioloctanoate From 1-heptene Using Bis(triphenylphosphine) Palladium(II) Chloride Tin(II) Chloride as Catalyst PART A. To a glass-lined reactor provided with stirring, heating, cooling and pressurizing means, charged with a stirred deoxygenated mixture of methyl isobutyl ketone (60 parts by weight) and ethyl mercaptan (9.3 parts by weight) is added under a nitrogen purge, anhydrous stannous chloride (0.95 parts by weight, 5 mmole), followed by 0.35 parts by weight of bis(triphenylphosphine)palladium (II) chloride complex* (0.5 mmole). Stirring of the yellow solution is continued for an additional 5-10 minutes at which time the autoclave is sealed, purged with nitrogen and carbon monoxide, and heated to 80° C under 100 psig of carbon monoxide for about 15 minutes. At the end of this time 4.9 parts by weight of 1-heptene (50 mmole) is added to the pressurized reactor and the carbon monoxide pressure raised to 2,000 psig. Periodically aliquots are removed for gas chromatographic (g.c.) analysis and after 6 hours, the reactor is cooled down, vented to reduce pressure and the 70 parts by weight of yellow liquid recovered and analyzed by g.c. Basis the 1-heptene charged, a yield of 61 mole % of ethyl thioloctanoate is obtained. The remainder of the product is found to be unreacted 1-heptene (1-heptene conversion is 78%) plus some branched thioester (ethyl thiodoctanoate selectivity = 82%).

*Prepared by the method of H. Itatani and J. C. Bailar, J. Amer. Oil Chem. Soc. 44 147 (1967)

EXAMPLE 2

Preparation of Methyl Thioloctanoate

In a run almost identical to that of the preceeding example, the process is repeated using the same proportions of reactants and reaction parameters, except that gaseous methyl mercaptan is substituted for ethyl mercaptan on a mole to mole basis and is added to the reaction mixture during pressuring of the reactor with carbon monoxide. Comparable conversion, selectivities and yields of the methyl thioloctanoate are obtained.

EXAMPLE 3

Preparation of Butyl Thioctanoate

Again the run of Example 1 is substantially repeated insofar as reaction conditions and reactants are concerned, except that n-butyl mercaptan is substituted for ethyl mercaptan on a mole by mole basis. Again comparable conversions, selectivities and yields are obtained.

EXAMPLE 4

Preparation of Phenyl Thioloctanoate

Once again the preparation is based upon that of Example 1 except that benzene thiol is substituted for ethyl mercaptan on a mole for mole basis. As in the preceding examples conversions, selectivities and yields are similar to those obtained in Example 1.

EXAMPLE 5

Preparation of Ethyl Thioloctanoate From 1heptene Using Homogeneous Platinum Catalysts-I.

Using the procedure, equipment, proportions and reaction parameters employed in Example 1, $PtCl_2(AsPh_3)_2$—10. $SnCl_2$ is substituted for the homogeneous palladium complex of Example 1 on a mole per mole basis. At the end of the reaction time the pressurized reactor is cooled, vented and analyzed using gas chromatography. A conversion of 10% of 1-heptene and a yield or ethyl thioloctanoate (based upon 1-heptene charged) of 3.5% is obtained. However, amongst the ethyl $C_8$ thioester products the selectivity to ethyl thioloctanoate is about 84%.

EXAMPLE 6

Preparation of Ethyl Thioloctanoate From 1-heptene Using Homogeneous Platinum Catalsts-II.

Again the same procedure, equipment, proportions and reaction parameters used in Example 1 are employed except that the catalyst complex $K_2PtCl_6$ —$10SnCl_2$ is substituted on a mole for mole basis for the homogeneous palladium catalyst of Example 1. A conversion of 12% of 1-heptene is obtained. The ethyl thioloctanoate yield is 2.6%, selectivity is 66%. The two runs appear to indicate that these two platinum catalysts, while having good selectivity, are much less effective than the palladium catalyst of the first example.

EXAMPLES 7 TO 11

Preparation of Ethyl Thioloctanoate Using Other Homogeneous Palladium Catalysts Table I lists other homogeneous palladium catalysts which may be substituted for $PdCl_2[P(C_6H_5)_3]_2$—$SnCl_2$ in the preparation of ethyl thioloctanoate as described in Example 1.

EXAMPLES 12 TO 16

Preparation of Ethyl Thioloctanoate — Effect of Temperature and Pressure Variations Table II shows data obtained when the $PdCl_2(PPh_3)_2$—$10SnCl_2$ catalyst system is employed for the synthesis of ethyl thioloctanoate from 1-heptene, using the procedure set forth in Example 1, but with the designated conditions of temperature and pressure.

EXAMPLE 17

The Preparation of Ethyl Thiolacrylate From Acetylene

An approximately equivolume mixture of carbon monoxide and acetylene is bubbled through a deoxygenated solution of 60 parts by weight of benzene, 10 parts by weight of ethanethiol, 0.95 parts by weight of stannous chloride (5.0 mmole), 0.35 parts by weight of bis(triphenylphosphine)palladium(II) chloride (0.5 mmole). After several hours at room temperature (21°–22°), a gas chromatographic analysis of the clear red solution confirmed the presence of ethyl thiolacrylate as the only detectable carboxylate product (acetone, an impurity in the acetylene feed, was also confirmed).

TABLE I

| EXAMPLE | CATALYST COMPOSITION |
|---|---|
| 7 | $PdCl_2[P(p-CH_3O.C_6H_4)_3]_2$-$SnCl_2$ |
| 8 | $PdCl_2[P(p-Cl.C_6H_4)_3]_2$-$SnCl_2$ |
| 9 | $PdCl_2[P(CH_3)_2C_6H_5]_2$-$SnCl_2$ |
| 10 | $PdCl_2[P(C_6H_5)_3]_2$-$GeCl_2$ |
| 11 | $PdCl_2[As(C_6H_5)_3]_2$-$SnCl_2$ |
| 12 | $PdCl_2[P(C_6H_5)_3]_2$-$SnCl_4$ |

TABLE II

| EXAMPLE | TEMP. (°C) | PRESSURE (PSIG) | 1-HEPTENE CONV. (%) | ETHYL THIOLOCTANOATE SELECTIVITY (%) | YIELD (%) |
|---|---|---|---|---|---|
| 13 | 20 | 3000 | <10 | 98 | 4.1 |
| 14 | 80 | " | 78 | 82 | 61 |
| 15 | 120 | " | <10 | 67 | 6.0 |
| 16 | 80 | 100 | <10 | 79 | 6.9 |

As the numerous examples and preceding discussion have documented, numerous advantages accrue from the practice of this invention both in its compositional aspect and its process aspects.

For example, a relatively large group of ligand stabilized noble metal-Group IVB metal halide catalysts are provided which were heretofore not known to be useful as catalysts for the conversion of unsaturated aliphatic substrates to their linear saturated and unsaturated, aliphatic thiol esters of carboxylic acids. These catalytic compositions offer the further advantage of being readily available by well known preparative procedures, and they have conversion efficacies even at substrate-to-catalyst molar ratios as high as 200 to 1, dependent upon the unsaturated aliphatic substrate, and the particular catalyst employed. Quite unexpectedly, the high activity of some palladium complexes is not followed by that of corresponding platinum complexes. This can be seen by the data obtained in the examples.

It its process aspect this invention provides a novel process for preparing linear saturated and unsaturated aliphatic, thiol esters of carboxylic acids. In addition, reaction times are rapid, the process lends itself to either batch or continuous operation, employing standard equipment. Further, selectivities to the linear saturated thiol esters are ordinarily of the order of 80% and higher.

A further advantage of the instant invention is that while in some respects reaction conditions are critical to success, in other respects the process offers flexibility. That is, numerous modifications and changes can be made in the choice of catalyst, nucelophilic coreactant and unsaturated aliphatic substrate, without departing from the inventive concept. The metes and bounds can best be determined by reading the claims which follow in light of the preceding specification.

What is claimed is:

1. A process for converting unsaturated aliphatic 1-alkenes containing 2 to 30 carbon atoms to linear saturated aliphatic thiol esters of carboxylic acids in good yield and relatively uncontaminated with non-linear thiol esters and by-products, by a process of:
   a. admixing each mole of 1-alkene to be converted to said thiol ester, with at least a catalytic amount of a palladium catalyst selected from the group consisting of:
   $PdCl_2[P(C_6H_5)_3]_2—SnCl_2$
   $PdCl_2[P(p-CH_3O.C_6H_4)_3]_2—SnCl_2$
   $PdCl_2[P(CH_3)_2C_6H_5]_2—SnCl_2$
   $PdCl_2[P(C_6H_5)_3]_2—GeCl_2$
   $PdCl_2[As(C_6H_5)_3]_2—SnCl_2$ and
   $PdCl_2[P(C_6H_5)_3]_2—SnCl_4$
   in the presence of at least a molar equivalent of mercaptan coreactant selected from the group consisting of saturated aliphatic mercaptans containing 1 to 10 carbon atoms, and
   b. pressurizing said reaction mixture with sufficient carbon monoxide to satisfy the stoichiometry of the carbonylation reaction;
   c. heating said pressurized reaction mixture to between 20° and 120°C, until conversion of the aliphatic 1-alkene substrate to said linear saturated aliphatic esters of carboxylic acids takes place, and
   d. isolating said saturated thiol ester contained therein.

2. The process of claim 1 wherein said catalyst is prepared in situ.

3. The process of claim 1 wherein said catalyst is added to the reaction mixture as a preformed complex.

4. The process of claim 1 in which the reaction mixture contains an inert solvent.

5. The process of claim 1 wherein the unsaturated aliphatic substrate is 1-heptena.

6. A process for converting aliphatic 1-alkynes containing 2 to 5 carbon atoms, to linear monounsaturated aliphatic thiol esters of carboxylic acids in good yield and relatively uncontaminated with non-linear thiol esters and by-products by a process of:
   a. admixing each mole of 1-alkyne aliphatic substrate to be converted to said thiol ester, with at least a catalytic amount of a palladium catalyst selected from the group consisting of:
   $PdCl_2[P(C_6H_5)_3]_2—SnCl_2$
   $PdCl_2[P(P-CH_3O.C_6H_4)_3]_2—SnCl_2$
   $PdCl_2[P(CH_3)_2C_6H_5[_2—SnCl_2$
   $PdCl_2[P(C_6H_5)_3]_2—GeCl_2$
   $PdCl_2[As(C_6H_5)_3]_2—SnCl_2$ and
   $PdCl_2[P(C_6H_5)_3]_2—SnCl_4$
   in the presence of at least a molar equivalent of mercaptan coreactant selected from the group consisting of aliphatic of mercaptans containing 1 to 10 carbon atoms and phenyl mercaptan;
   b. pressurizing said reaction mixture with sufficient carbon monoxide to satisfy the stoichiometry of the carbonylation reaction;
   c. heating said pressurized reaction mixture to between 20° and 120°C, until conversion of the aliphatic 1-alkyne substrate to said linear monounsaturated aliphatic esters of carboxylic acids takes place, and
   d. isolating said mono-unsaturated thiol ester contained therein.

7. The process of claim 6 wherein the unsaturated substrate is acetylene.

* * * * *